US010935480B1

(12) United States Patent
Nourbakhsh et al.

(10) Patent No.: US 10,935,480 B1
(45) Date of Patent: Mar. 2, 2021

(54) OPTICAL-PARTICLE SENSOR HEAD

(71) Applicant: Airviz Inc., Pittsburgh, PA (US)

(72) Inventors: Illah Nourbakhsh, Pittsburgh, PA (US); Dömötör Gulyás, Pittsburgh, PA (US); Michael Taylor, Pittsburgh, PA (US); Charles D. Litton, Pittsburgh, PA (US)

(73) Assignee: AIRVIZ INC., Pittsburgh, PA (US)

( * ) Notice: Subject to any disclaimer, the term of this patent is extended or adjusted under 35 U.S.C. 154(b) by 14 days.

(21) Appl. No.: 16/583,684

(22) Filed: Sep. 26, 2019

Related U.S. Application Data

(60) Provisional application No. 62/736,846, filed on Sep. 26, 2018.

(51) Int. Cl.
*G01N 33/00* (2006.01)
*G01N 15/02* (2006.01)
*G01N 15/06* (2006.01)
*G01N 21/47* (2006.01)

(52) U.S. Cl.
CPC ............ *G01N 15/06* (2013.01); *G01N 21/47* (2013.01); *G01N 33/0063* (2013.01); *G01N 2015/0238* (2013.01)

(58) Field of Classification Search
CPC .... G01N 15/06; G01N 21/47; G01N 33/0063; G01N 2015/0238; G01N 21/15; G01N 21/31; G01N 2021/157; G01N 21/0303; G01N 21/05; G01N 15/1459
USPC ... 356/432, 343, 38, 339, 336, 436, 73, 244, 356/246, 438
See application file for complete search history.

(56) References Cited

U.S. PATENT DOCUMENTS

| | | | | |
|---|---|---|---|---|
| 3,431,423 A * | 3/1969 | Keller | ................ | G01N 15/1429 250/574 |
| 4,273,443 A * | 6/1981 | Hogg | ................. | G01N 15/1436 250/574 |
| 5,043,591 A * | 8/1991 | Ludlow | .............. | G01N 15/1434 250/574 |
| 5,089,714 A * | 2/1992 | Ludlow | .............. | G01N 15/1456 250/574 |
| 5,471,299 A * | 11/1995 | Kaye | ................... | G01N 15/1436 356/336 |
| 6,084,844 A | 7/2000 | Takeda | | |
| 7,921,436 B2 | 4/2011 | Shimizu et al. | | |
| 8,520,221 B2 | 8/2013 | Lohmann | | |
| 8,534,116 B2 * | 9/2013 | Wang | ................. | G01N 15/0205 73/28.01 |
| 8,654,329 B2 | 2/2014 | Tucker et al. | | |
| 9,448,105 B2 | 9/2016 | Harpin et al. | | |
| 9,612,200 B2 | 4/2017 | Fujita et al. | | |
| 9,824,786 B2 | 11/2017 | Sotirelis et al. | | |

(Continued)

FOREIGN PATENT DOCUMENTS

WO WO 2016/067484 5/2016
WO WO 2018/104153 6/2018
(Continued)

*Primary Examiner* — Isiaka O Akanbi

(57) ABSTRACT

An optical-particle sensor head comprises an electromagnetic radiation source to transmit electromagnetic radiation toward the detection chamber; one or more baffles, between the light source and the detection chamber, to restrain a spread of the electromagnetic radiation from the electromagnetic radiation source; and at least two off-angle photosensors.

18 Claims, 4 Drawing Sheets

(56) References Cited

U.S. PATENT DOCUMENTS

| | | |
|---|---|---|
| 9,857,301 B1 | 1/2018 | Nourbakhsh et al. |
| 9,983,236 B2 | 5/2018 | Bohnert et al. |
| 2009/0122315 A1* | 5/2009 | Jarrell ................ G01N 15/0205 |
| | | 356/343 |
| 2017/0241893 A1* | 8/2017 | Walls ................ G01N 15/1436 |

FOREIGN PATENT DOCUMENTS

| | | |
|---|---|---|
| WO | WO 2018/104154 | 6/2018 |
| WO | WO 2018/222980 | 12/2018 |
| WO | WO 2019/167485 | 9/2019 |

\* cited by examiner

OPTICAL-PARTICLE SENSOR HEAD

PRIORITY CLAIM

The present invention claims priority to U.S. provisional application Ser. No. 62/736,846, filed Sep. 26, 2018, which is incorporated herein by reference in its entirety.

FIELD OF INVENTION

The present invention relates to the geometric design of an optical-particle sensor head enabling the use of low-cost laser diode or LED light sources and photodiode discrete components to achieve very high sensitivity and signal-to-noise ratio detection of particulate matter in the air through light scattering measurements.

BACKGROUND OF THE INVENTION

Significant bodies of research indicate that cumulative, personal exposure to fine particulates and ultrafine particulates are strongly correlated with pulmonary disease and cardiovascular disease, as discussed in U.S. Pat. No. 8,147,302. In addition, statistically significant correlations have now been discovered between exposure to particles with diameters less than 2.5 μm ($PM_{2.5}$) by pregnant women and the onset of autism and attention deficit hyperactivity disorder in children born to exposed pregnant women. Daily exposure in the residential home and while carrying mobile devices represents a large portion of a person's overall exposure profile to air pollution. Therefore, direct measurement and reporting of home air pollution and mobile exposure can provide valuable insight. Such insight can be used for mitigation of overall pollution exposure in order to maximize long-term and short-term health.

Existing low-cost devices suitable for integration into retail products suffer from lack of linearity and lack of value agreement, inability to detect ultrafine particles, high power budgets that make mobile applications impractical, and poor communication interfacing to mobile devices. More high-quality particle detection devices suffer from very high cost due to the need for high-end electronic discrete components, as the properties of the light source and photodetector or photodetectors bear greatly on the overall system sensitivity and performance.

In general, conventional sensor head designs for particle detection do not achieve a very high quality of performance without relatively expensive electronic discrete components. Maintaining this quality of performance while using lower-cost discrete electronic components to reduce the cost of sensor heads would be useful and encourage overall air quality monitoring.

SUMMARY OF THE INVENTION

In one general aspect, the present invention is directed to an optical particle-detection sensor head including an internal geometry designed to improve detection of particulate matter in the air. In particular, the housing of the sensor head can be physically designed so that it is specifically suited to optimizing signal-to-noise ratio and sensitivity while avoiding the need for prohibitively expensive photodetectors and light sources. Compared to conventional devices, the present invention can improve light control, noise control, and relative cost. These and other benefits of the present invention are apparent from the description herein.

BRIEF DESCRIPTION OF THE DRAWINGS

Various embodiments of the present invention are described herein by way of example in connection with the following figures.

DESCRIPTION

Figure 1:
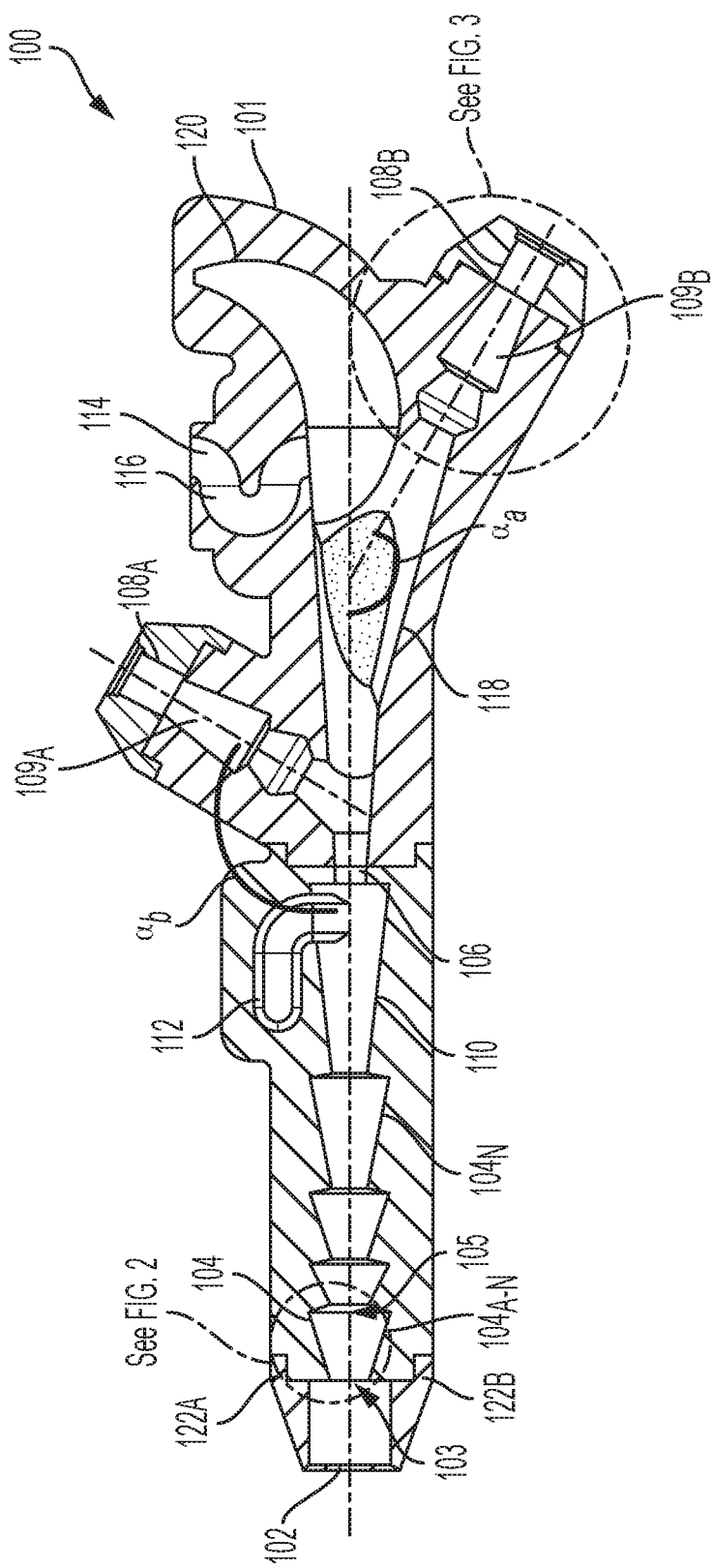
FIG. 1 is a cross sectional view of an optical-particle sensor head according to one non-limiting embodiment of the present disclosure.

An optical-particle-detection sensor head, as shown in FIGS. 1 through 4, includes an internal geometry designed to improve detection of particulate matter in the air. Specifically, the optical-particle-detection sensor head uses, in one embodiment, a "Rayleigh Horn" geometry as a light trap to eliminate multipath interference from laser diode signals downstream of sensing interrogation spaces, thereby improving light control. When light propagates from a source of light or electromagnetic radiation, the emitted photons are directed towards the horn, which confines the photons within an internal volume, thereby causing each photon to reflect between interior walls of the horn instead of reflecting back through the optical-particle-detection sensor head. Accordingly, the horn not only captures the photons emitted by the light source, but it also progressively attenuates the energy of each photon it captures. The internal walls of the horn absorb the energy of each photon as it reflects off the internal walls, remaining within the volume of the horn itself. As such, the sensor head prevents or reduces instances of propagated light reflecting back to the receiving sensor. For example, a sensor can be a photodetector such as a photodiode. This can result in a better signal-to-noise ratio.

To improve noise control, the optical particle-detection sensor head uses, in various embodiments, a specific geometric configuration of the housing and detection chamber to address radially asymmetric reflection of the photons propagated from the light source. In particular, low-cost laser diodes and other light sources do not necessarily create a point, or even spherical, point-spread function in their light output, even after collimation. Rather, such light sources have a radially asymmetric footprint. Noise can result from photons reflecting into the receiving photodetectors at undesirable angles, which are angles other than the air particle scattering angles corresponding to the location of the photodetectors. In order to eliminate noise from non-collinear and other unwanted angles of emission, the present invention employs, in various embodiments, geometric aperturing and light absorbing geometry between the laser diode output and the collimating lens, as well as specific geometric solutions to laser light scattering throughout the possible light pathways. The specific geometric solutions include particular angled surfaces designed to prevent or reduce reflection of light into the receiving photodiodes.

The optical particle-detection sensor head can also advantageously include multiple sensors (e.g. photodetectors). Having multiple photodetectors at different incident angles rather than merely a single photodetector arrangement can enable better discrimination and reporting on the size of particles in the incoming air particle flow, at an affordable cost point. Scattered light reflecting off particles can vary in signal strength depending on the incident or scatter angle of photodetection. The sensor head can include multiple photodetectors, positioned at different incident or scatter angles, which enables direct estimation of particle size distribution. Such direct estimation functionality can be valuable for low-cost air pollution sensors. Additional details about optical particle sensors with multiple off-angle photosensors is described in PCT Application No. PCT/US18/35,582, filed Jun. 1, 2018, which is incorporated herein by reference in its entirety.

Referring now to FIG. 1, a cross-sectional side view of the optical-particle sensor head 100 is depicted in accordance with one non-limiting embodiment of the present invention. At the left-most region of FIG. 1, a light source 102 is shown. For example, the light source 102 can be a light emitting diode (LED), laser, or other suitable source of light or electromagnetic radiation. The light source 102 emits photons through a laser diode emission region (e.g., detection chamber) 106. The light source 102 can be coupled to one or more baffles $104_{A-N}$. Although the baffles $104_{A-N}$ of FIG. 1 are shown with conical cross-section beveling in FIG. 1, the present disclosure further contemplates baffles $104_{A-N}$ of any suitable shape for restraining the flow and otherwise constraining the spread of photons emitted from the light source 102 in a particular direction. Additionally, the baffles $104_{A-N}$ can progressively vary in size along the direction from the light source 102 to the detection chamber 106, as shown in FIG. 1 to enhance the restriction of photon flow. For example, in the non-limiting embodiment of FIG. 1, each baffle $104_{A-N}$ defines a cavity with an input aperture 103 and an output aperture 105. The input aperture 103 of each baffle $104_{A-N}$ can be larger than the output aperture 105 of each baffle $104_{A-N}$ to ensure that photons can more easily flow from the light source 102 into the optical-particle sensor head, but experience more resistance if they reflect and attempt to flow back towards the light source 102. Additionally and/or alternatively, the input aperture 103 and output aperture 105 of the last baffle $104_N$ can be smaller than the input aperture 103 and output aperture 105 of the first baffle $104_A$ to further facilitate the flow of photons away from the light source 102 and into the optical-particle sensor head.

In further reference to FIG. 1, air enters a detection chamber 106 through an air inlet 112, flows through the detection chamber 106, where it can scatter light from the light source 102, and exits through an air outlet 114. The optical-particle sensor head 100 of FIG. 1 simultaneously requires access to outside air to provide particulate counts and loading estimates, as well as a reduction of external noise that could disrupt the accuracy of the measurements. Accordingly, the air inlet 112 and outlet 114 can be configured with a specific geometry that enables access to outside air while minimizing the chance of external light pollution as well as incidental internal multipath noise through the internal cavities of the housing 101. For example, the housing 101 can include serpentine, bent air channels 116 as shown in FIG. 1, to prevent or reduce pollution and noise. In some non-limiting embodiments, the air particle flow can be further facilitated by providing fans adjacent to one or more of the air inlet or outlet 112, 114.

Still referring to FIG. 1, once airflow enters the detection chamber 106, the stream of emitted photons can be exposed to particulate in the air. Accordingly, some of the photons propagated through the detection chamber 106 can reflect off particles in the airflow towards the sensors or photodetectors (e.g., photodiodes) $108_A$, $108_B$. The optical-particle sensor head 100 can further include a collimating lens 110 positioned to the right of the repeated optical baffles $104_{A-N}$. The collimating lens 110 can focus the remaining laser light specifically at the fine focal point required for the interrogation of scattering in the detection chamber 106, rather than pursuing infinite-focal length collimation with an imperfect laser diode. The photons can be scattered past the fine focal point so that the photodetectors $108_A$, $108_B$ can capture the scattered photons at the corresponding scattering angle. Accordingly, the photons are scattered by air particles flowing through the air inlet 112 and out through the air outlet 114.

In further reference to FIG. 1, the sensors or photodetectors $108_A$, $108_B$ can be configured at desired scatter angles $\alpha_a$, $\alpha_b$ relative to the direction of the light energy from the light source 102. In most cases, a scatter angle $\alpha_a$, $\alpha_b$ between 15 degrees (°) and 90° is acceptable to capture sufficient photons to take a measurement. However, the present disclosure contemplates alternate scatter angles $\alpha_a$, $\alpha_b$ depending on the desired application and/or outcome. For example, in the non-limiting example of FIG. 1, the detection chamber 106 includes photodetectors $108_A$, $108_B$ that are configured at a scatter angle $\alpha_a$, $\alpha_b$ of 60° and 30°, respectively. Additionally, the optical-particle sensor head 100 can further include one or more baffles $109_A$, $109_B$ ... $109_N$ in between the detection chamber 106 and the sensor or photodiodes $108_A$, $108_B$ to provide supplementary restraint of the emitted photons towards the photodiodes $108_A$, $108_B$. The inclusion of such baffles $109_A$, $109_B$ ... $109_N$ prevents photons from reflecting back into the detection chamber 106 and subsequently scattering of particulate in the air sample a second time, thereby reducing indirect scatter along the scatter angle $\alpha_a$, $\alpha_b$ and protecting the sensors $108_A$, $108_B$ from unwanted such noise.

Still referring to FIG. 1, laser diode light from the light source 102 can be captured after passing through the detection chamber 106 to minimize follow-on interference through reverse reflections. The detection chamber region 118 can have a flat upper surface to limit the height of the housing 101. To capture the photons that pass through the detection chamber region 118, the sensor head 100 includes a horn 120 to trap all or most photons exiting the detection chamber region 118. As such, the probability of high-intensity reverse reflection can be eliminated or significantly reduced. The horn 120 can trap photons within its interior perimeter. In particular, the photons trapped within the horn 120 can continually reflect off the internal walls of the horn 120 so as to attenuate while remaining within the interior perimeter of the horn 120. The horn 120 can be a suitable geometry, such as a Raleigh-style horn 120.

In further reference of FIG. 1, the detection chamber 106 can be configured with a specific geometry to optimize the noise-eliminating space and enhance the interrogation of optical scattering by particles in the airflow while preserving the possibility of using economical components. For example, the optical-particle sensor head 100 of FIG. 1 includes geometrical features, such as the horn 120, which are inherently designed to channel photons and reduce indirect scatter, thereby enabling the use of cheaper components that otherwise result in an unacceptable amount of indirect scatter. For example, the collimating lens 110 of FIG. 1 can be a low-cost, plastic unit. The light source 102 of FIG. 1 can also be inherently less-collimating, such as an LED. Additionally, the housing 101 can be inexpensively produced, including injection molding and/or 3D-printed plastic. Accordingly, the optical-particle sensor head 100 of FIG. 1 can reduce the overall cost sensor while preserving performance and accuracy.

Still referring to FIG. 1, the optical-particle sensor head 100 can be employed to produce accurate particulate counts and loading estimates of external airflow samples. Particulate counts and loading estimates can be determined based on comparing the corresponding scattering intensity output signals generated by photodetectors $108_A$, $108_B$ to baseline information. Accordingly, the photodetectors $108_A$, $108_B$ can be operationally coupled to a processor (e.g., microprocessor, controller, field programmable gate array, digital signal processor etc.) that is programmed to perform the comparison of output signals to the baseline information. The thresholds can be stored in a memory device (e.g., RAM, ROM etc.) coupled to the processor. Because baseline photodiode measurement values are critical to disambiguating background noise from true signal, the sensor head 100 can include a processor configured to power down the laser diode 102, thereby enabling photodiode collection of measurements of background, baseline noise for calibration.

In further reference of FIG. 1, the alignment of the laser diode beam can be important to the operation of the sensor head 100. Baffle $104_{A-N}$ designs at the source end of the sensor head 100 can be provided to assist with alignment. Moreover, registration shoulders 122A, 122B at the laser diode attachment point enable the laser diode module to be aligned with greater repeatability, reducing the need for inter-device calibration. Additionally, a major shortcoming of existing scattered-light sensor head designs involves the agglomeration of dust on interior surfaces of the housing 101, occluding or interfering with scattered light sensing in the detection chamber 118. The sensor head 100 of the present invention can reduce such aggregation of dust. The housing 101 can include a large detection chamber 118 volume, in which dust can be both less likely to collect on surfaces nearby, and less reactive with the dynamics of measurement by the photodetectors $108_A$, $108_B$. This can be particularly true because of the wall geometry of the housing 101.

Figure 2:
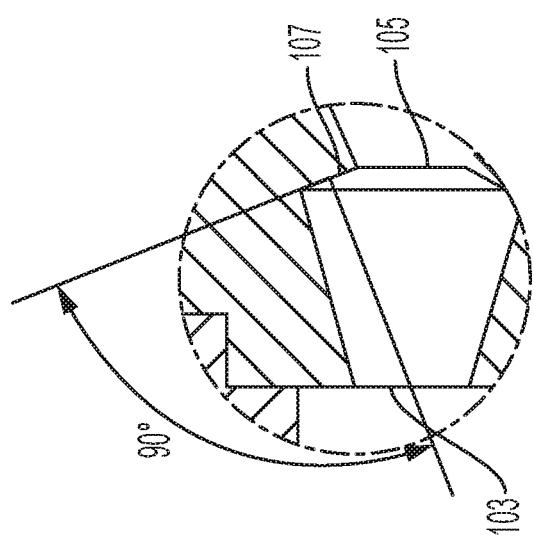
FIG. 2 is a cross sectional view of a baffle of the optical-particle sensor head of FIG. 1.
Figure 3:
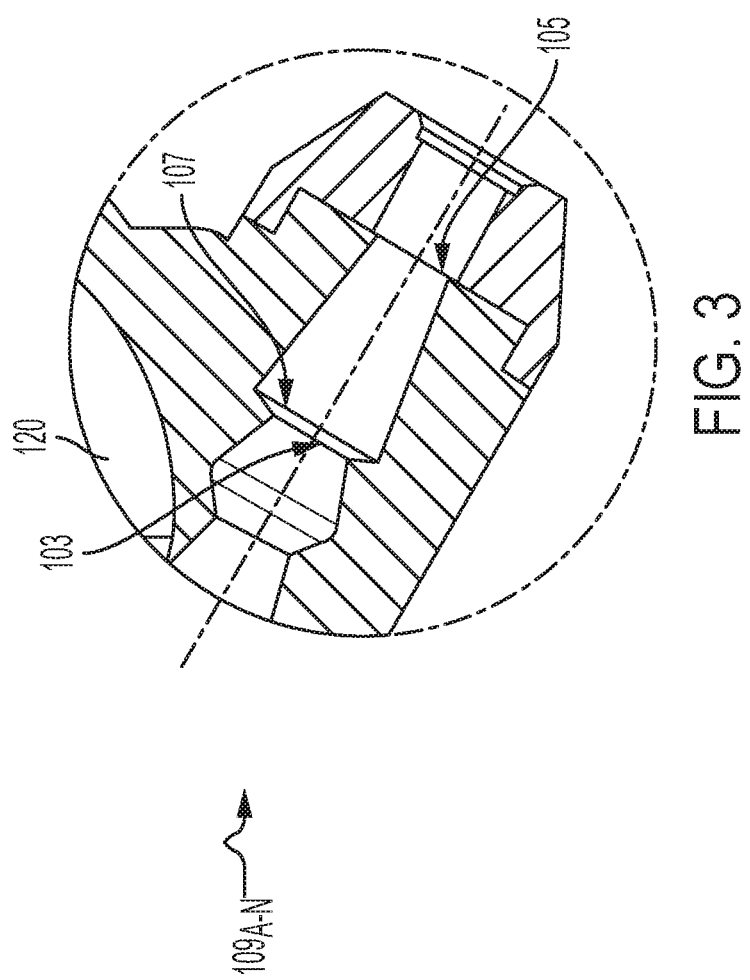
FIG. 3 is a cross sectional view of another baffle of the optical-particle sensor head of FIG. 1.

Referring now to FIGS. 2 and 3, cross-sectional side views of the baffles $104_{A-N}$, $109_{A-N}$ used by the optical-particle sensor head 100 of FIG. 1 are respectively depicted in accordance with at least one non-limiting embodiment of the present disclosure. As previously discussed, a baffle $104_{A-N}$ can iteratively reduce spread of the light energy from the light source 102, capturing and returning high spread emissions back to the source direction (light source 102). In other words, the reflection of some or all of the photons traveling through the baffles $104_{A-N}$ can be controlled to prevent or reduce reflection of photons onto the sensors or photodetectors $108_A$, $108_B$ such that noise corresponding to reflected photons can be avoided. The input aperture 103 of each baffle $104_{A-N}$ can be larger than the output aperture 105 of each baffle $104_{A-N}$ to ensure that photons can more easily flow from the light source 102 into the optical-particle sensor head, but experience more resistance if they reflect and attempt to flow back towards the light source 102. Additionally and/or alternatively, the input aperture 103 and output aperture 105 of the last baffle $104_N$ can be smaller than the input aperture 103 and output aperture 105 of the first baffle $104_A$ to further facilitate the flow of photons away from the light source 102 and into the optical-particle sensor head. Accordingly, the baffles $104_{A-N}$, $109_{A-N}$ can configured to ensure optical invisibility to the light source 102 from any point along any input aperture, while maintaining visibility along any point of any output aperture. For example, the conical surfaces of the baffles $104_{A-N}$ of the optical-particle sensor head 100 can be invisible relative to the input aperture.

In further reference of FIGS. 2 and 3, the baffles $104_{A-N}$ and/or $109_{A-N}$ can include a knife-edge 107 or near knife-edge apertures to maximize discontinuous changes in angle, as required for the aforementioned light-control geometries. The apertures 103, 105, aperture edges 107 and conical baffles $104_{A-N}$ and/or $109_{A-N}$ can be specifically configured to work in conjunction to ensure that no single-bounce stray light can pollute sensed particle scattering responses. Instead, the stray light can be absorbed into the interior walls or reflected in a manner that does not contact photodiodes $108_A$, $108_B$. In this way, background noise in the optical-particle sensor head and/or system as a whole can be minimized.

Figure 4:
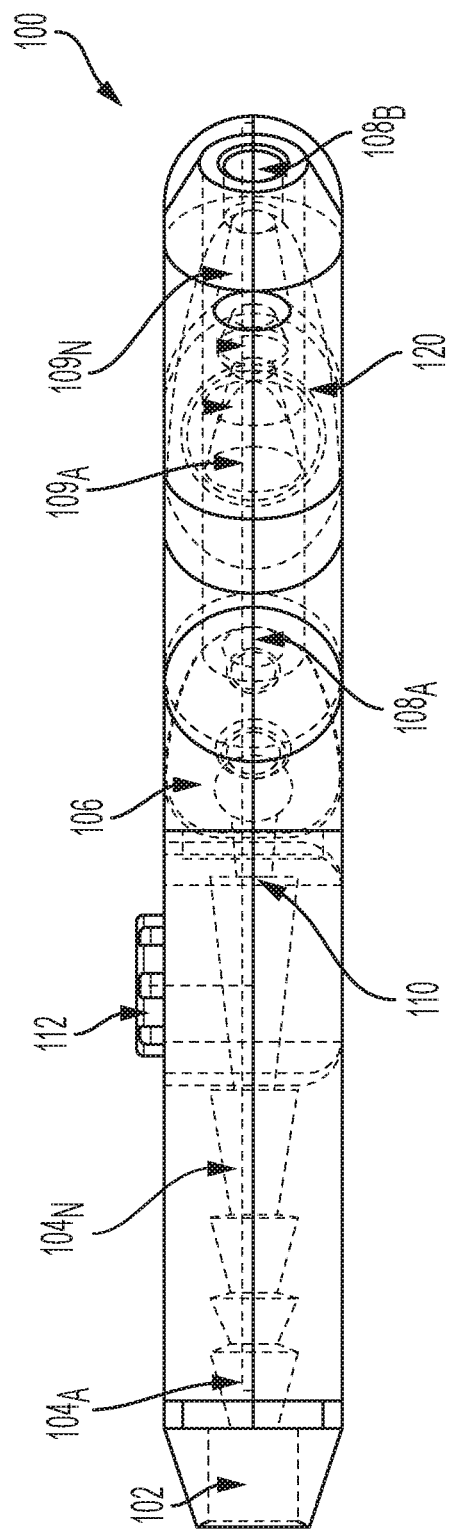
FIG. 4 is a top view of the optical-particle sensor head of FIG. 1.

Referring now to FIG. 4, a top view of the optical-particle sensor head 100 of FIG. 1 is depicted in accordance with at least one non-limiting embodiment of the present disclosure. FIG. 4 offers an alternate view of the geometries of the baffles $104_{A-N}$, $109_{A-N}$, detection chamber 106, and horn 120, including their widths relative to one another as well as housing 101 located near the light source 102. As shown in FIG. 4, the interior surface of the housing 101 can be configured to encourage initial reflection of photons towards the sensors or photodetectors $108_A$, $108_B$, subsequent or indirect reflection of photons away from the sensors or photodetectors $108_A$, $108_B$ and capture of indirectly reflected photons in horn 120. FIG. 4 further provides a detailed view of the horn 120 as well as a portion of the detection chamber 106 proximal to the sensors or photodetector $108_A$, $108_B$. As shown in FIG. 4, photons can be reflected away from the sensors or photodetectors $108_A$, $108_B$ towards either the opposite wall or the light source 102, thereby advantageously improving the signal to noise ratio of measurements taken by the sensors or photodetector $108_A$, $108_B$.

The examples presented herein are intended to illustrate potential and specific implementations of the present invention. It can be appreciated that the examples are intended primarily for purposes of illustration of the invention for those skilled in the art. No particular aspect or aspects of the examples are necessarily intended to limit the scope of the present invention. Further, it is to be understood that the figures and descriptions of the present invention have been simplified to illustrate elements that are relevant for a clear understanding of the present invention, while eliminating, for purposes of clarity, other elements. While various embodiments have been described herein, it should be apparent that various modifications, alterations, and adaptations to those embodiments can occur to persons skilled in the art with attainment of at least some of the advantages. The disclosed embodiments are therefore intended to include all such modifications, alterations, and adaptations without departing from the scope of the embodiments as set forth herein.

What is claimed is:

1. An optical-particle detection device comprising:
   a light source configured to emit a plurality of photons in a direction of emission;
   a sensor head coupled to the light source, wherein the sensor head comprises:
   a sensor oriented at a scatter angle relative to the direction of emission;
   an inlet configured to receive an air sample comprising a plurality of particles;
   a collimating lens configured to focus the plurality of photons through the air sample such that at least one photon of the plurality of photons scatters off of at least one particle of the plurality of particles;

a detection chamber coupled to the collimating lens and the sensor, wherein the detection chamber defines an internal cavity configured to direct a scattered photon towards the sensor;

a capture chamber coupled to the detection chamber, wherein the capture chamber is configured to receive a photon from the detection chamber, and wherein the capture chamber defines an internal cavity configured to control the reflection the photon such that the photon does not return to the detection chamber and a first baffle positioned between the light source and the collimating lens, wherein the first baffle defines a cavity comprising an input aperture and an output aperture, and wherein the input aperture of the first baffle is larger than the output aperture of the first baffle.

2. The optical-particle detection device of claim 1, further comprising a second baffle positioned between the light source and the first baffle, wherein the second baffle comprises an input aperture and an output aperture, and wherein the input aperture of the second baffle is larger than the output aperture of the first baffle.

3. The optical-particle detection device of claim 2, further comprising a third baffle positioned between the detection chamber and the sensor, wherein the third baffle comprises an input aperture and an output aperture, and wherein the input aperture of the third baffle is larger than the output aperture of the third baffle.

4. The optical-particle detection device of claim 3, further comprising a fourth baffle positioned between the third baffle and the sensor, wherein the fourth baffle comprises an input aperture and an output aperture, wherein the input aperture of the third baffle is larger than the output aperture of the fourth baffle.

5. The optical-particle detection device of claim 4, wherein at least one of the input aperture of the first baffle, the output aperture of the first baffle, the input aperture of the second baffle, the output aperture of the second baffle, the input aperture of the third baffle, the output aperture of the third baffle, the input aperture of the fourth baffle, or the output aperture of the fourth baffle comprises a knife-edge.

6. The optical-particle detection device of claim 5, wherein at least one of the first baffle, the second baffle, the third baffle, or the fourth baffle comprises a conical shape.

7. The optical-particle detection device of claim 6, wherein the internal cavity of the capture chamber comprises a Rayleigh horn.

8. The optical-particle detection device of claim 1, further comprising a second sensor coupled to the detection chamber, wherein the second sensor is oriented at a second scatter angle relative to the direction of emission, and wherein the internal cavity of the detection chamber is further configured to direct a photon from the plurality of photons that has scattered off of the particle towards the second sensor.

9. The optical-particle detection device of claim 1, wherein the scatter angle is thirty degrees and the second scatter angle is sixty degrees.

10. The optical-particle detection device of claim 1, wherein the collimating lens comprises a plastic material.

11. The optical-particle detection device of claim 1, wherein the light source comprises a light emitting diode.

12. An optical-particle sensor head for use with an optical-particle detection device, comprising:
a first sensor;
a second sensor;
an inlet configured to receive a sample of air comprising a plurality of particles;
a collimating lens configured to receive a beam of photons, wherein the collimating lens is further configured to focus the beam of photons in a direction of emission;
a detection chamber in fluid communication with the inlet and coupled to the collimating lens, wherein the detection chamber is configured to channel the sample of air from the inlet such that at least one photon of the beam of photons scatters off at least one particle of the plurality of particles, and wherein the detection chamber comprises:
a first channel coupled to the first sensor, wherein the first channel is oriented at a first scatter angle relative to the direction of emission;
a second channel coupled to the second sensor, wherein the second channel is oriented at a second scatter angle relative to the direction of emission; and
an internal cavity geometrically configured to direct a scattered photon into either the first channel or the second channel;
a capture chamber coupled to the detection chamber, wherein the capture chamber is configured to receive a photon of the beam of photons from the detection chamber, and wherein the capture chamber comprises an internal cavity geometrically configured such that the received photon reflects off the walls of the internal cavity and does not return to the detection chamber; and
a first baffle coupled to the collimating lens, wherein the first baffle defines a cavity comprising an input aperture and an output aperture, and wherein the input aperture of the first baffle is larger than the output aperture of the first baffle.

13. The optical-particle sensor head of claim 12, wherein the internal cavity of the capture chamber comprises a Rayleigh horn.

14. The optical-particle sensor head of claim 12, wherein the first scatter angle is thirty degrees and the second scatter angle is sixty degrees.

15. The optical-particle sensor head of claim 2, wherein the first channel comprises a second baffle positioned between the internal cavity of the detection chamber and the first sensor, wherein the second baffle comprises an input aperture and an output aperture, and wherein the input aperture of the second baffle is larger than the output aperture of the second baffle.

16. The optical-particle sensor head of claim 15, wherein the second channel comprises a third baffle positioned between the internal cavity of the detection chamber the second sensor, wherein the third baffle comprises an input aperture and an output aperture, and wherein the input aperture of the third baffle is larger than the output aperture of the third baffle.

17. The optical-particle sensor head of claim 15, further comprising an outlet through which the sample of air can leave the optical-particle sensor head, wherein the inlet comprises a serpentine channel, wherein the outlet comprises a serpentine channel, and wherein the serpentine channels of both the inlet and the outlet are configured to reduce an amount of optical pollution and noise that enters the detection chamber.

18. An air-particle detection system comprising:
a light source configured to emit an adjustable beam of photons;

a sensor head in communication with the light source, wherein the sensor comprises:
   a photodiode configured to convert a photon of the beam of photons into an output signal;
   an inlet configured to receive an air sample comprising a plurality of particles;
   a collimating lens configured to focus the beam of photons into the air sample such that at least one photon of the beam of photons scatters off at least one particle of the plurality of particles;
   a detection chamber configured to direct a scattered photon towards the photodiode;
   a capture chamber configured to retain a photon of the beam of photons received from the detection chamber within an internal cavity; and
   a first baffle coupled to the collimating lens, wherein the first baffle defines a cavity comprising an input aperture and an output aperture, and wherein the input aperture of the first baffle is larger than the output aperture of the first baffle;
a data storage device configured to store baseline information; and
a processor in communication with the light source, the sensor head, and the data storage device, wherein the processor is configured to:
   receive the output signal from the photodiode;
   interpret a particle count based on the output signal received from the photodiode;
   compare the particle count to the baseline information stored in the data storage device; and
   control the light source to adjust the beam of photons based on the comparison of the particle count and the baseline information.

* * * * *